United States Patent [19]

Ciervo

[11] Patent Number: 5,451,220
[45] Date of Patent: Sep. 19, 1995

[54] BATTERY OPERATED MULTIFUNCTION ULTRASONIC WIRE FOR ANGIOPLASTY

[75] Inventor: Donald J. Ciervo, Merrick, N.Y.

[73] Assignee: Microsonic Engineering Devices Company, Inc., Merrick, N.Y.

[21] Appl. No.: 290,064

[22] Filed: Aug. 15, 1994

[51] Int. Cl.⁶ .................................................. A61B 17/32
[52] U.S. Cl. .................................... 606/1; 606/169; 604/22
[58] Field of Search ................ 604/21, 22, 52; 606/1, 606/170, 171, 33, 169; 607/97

[56] References Cited

U.S. PATENT DOCUMENTS

| | | | |
|---|---|---|---|
| 3,584,327 | 6/1971 | Murry | 606/169 |
| 5,112,300 | 5/1992 | Ureche | 604/22 |
| 5,163,421 | 11/1992 | Bernstein | 606/169 X |
| 5,195,954 | 3/1993 | Schnepp-Pesch et al. | 604/22 |
| 5,382,228 | 1/1995 | Nita et al. | 604/22 |

*Primary Examiner*—Peter A. Aschenbrenner
*Attorney, Agent, or Firm*—Charles E. Baxley

[57] ABSTRACT

An ultrasonic angioplasty apparatus includes an ultrasonic generator which is coupled to a segmented wire that includes a relatively stiff portion, a more flexible portion and an extremely flexible portion. Ultrasonic energy, which is coupled to an end of the relatively stiff portion, reduces friction between the wire and an interior arterial vessel wall and whip-like motion of the extremely flexible portion allows the wire to pass high grade occlusions and plaque build-ups. The ultrasonic generator has a selectable range of operating frequencies which allow whip-like motion of the end of the wire, or alternatively directing ultrasonic cavitational forces into vessel wall to remove plaque build-up.

17 Claims, 3 Drawing Sheets

BATTERY OPERATED MULTIFUNCTION ULTRASONIC WIRE FOR ANGIOPLASTY

BACKGROUND OF INVENTION

1. Field of Invention

This invention relates generally to an ultrasonic surgical system and more particularly relates to a battery operated multifunction ultrasonic wire for angiograms, angioplasty and similar vascular procedures.

2. Description of the Prior Art

The prior art related to apparatus for angiograms, angioplasty and similar vascular procedures, includes various types of guide wires typically for guiding a balloon catheter to the location of a clot and/or plaque forming a constriction or blockage within a vessel. One of the difficulties associated with such procedures is difficulty of passing the guide wire through the vessel, because of friction between the guide wire and a wall of the vessel as well as getting past a lesion or past the blockage of the vessel.

SUMMARY OF INVENTION

In accordance with present invention, there is provided a battery operated multi-function ultrasonic wire for angiograms, angioplasty and similar vascular procedures, which includes an ultrasonic generator and a segmented wire. The segmented wire comprises a relatively stiff portion, which is joined to a somewhat more flexible portion, which in turn is joined to an extremely flexible end portion. The relatively stiff portion is coupled directly to the ultrasonic generator and application of ultrasonic energy thereto decreases frictional forces between the segmented wire and arterial vessel wall, thereby facilitating insertion of the segmented wire and also causing a whip-like motion of the end portion which enables the wire to cross high grade lesions.

The ultrasonic generator has a selector switch which allows choice between two modes of operation. In the first mode the ultrasonic energy decreases friction between the segmented wire and the vessel wall. In the second mode the ultrasonic energy enables a rasp-like portion of the segmented wire which is located on the distal end of the second portion of the wire to file away portions of plaque or other build-ups.

It is, therefore, a principal object of the present invention to provide a battery operated multifunction ultrasonic wire, particularly well suited for angioplasty, which utilizes ultrasonic energy to facilitate passage of the guide wire through the vessel.

Another object of the present invention is to provide a battery operated multifunction ultrasonic wire, particularly well suited for angioplasty, which is a capable of applying cavitational energy to clear an occlusion in an artery.

Still another object of the present invention is to provide a battery operated multifunction ultrasonic wire, particularly well suited for angioplasty, which includes a rasp-like portion for removal of plaque or other build-up and dilation of the artery.

A further object of the present invention is to provide a battery operated multifunction ultrasonic wire, particularly well suited for angioplasty, which includes a disposable ultrasonic generator to eliminate need for sterilization.

Still a further object of the present invention is to provide a battery operated multifunction ultrasonic wire, particular well suited for angioplasty, which provides both longitudinal motion along its length to facilitate passage of the guide wire through vessel lumens and transverse motion of a tip portion which aids in passing the wire past a high grade occlusion or plaque build-up.

Yet a further object of the present invention is to provide a battery operated multifunction ultrasonic wire, particularly well suited for angioplasty, which is capable of a first mode of operation wherein it decreases friction between the guide wire and the wall of the vessel and a second mode of operation wherein ultrasonic motion is used to prune plaque build-up from the wall of the vessel.

Yet another object of the present invention is to provide a battery operated multifunction ultrasonic wire, particularly well suited for angioplasty, which comprises a relatively small number of components resulting in highly reliable operation.

BRIEF DESCRIPTION OF DRAWINGS

The foregoing and other objects and many of the attendant advantages of this invention will be appreciated readily as they become understood better by reference to a following detailed description of certain preferred embodiments considered in connection with accompanying drawings in which.

DETAILED DESCRIPTION OF PREFERRED EMBODIMENT

Figure 1:
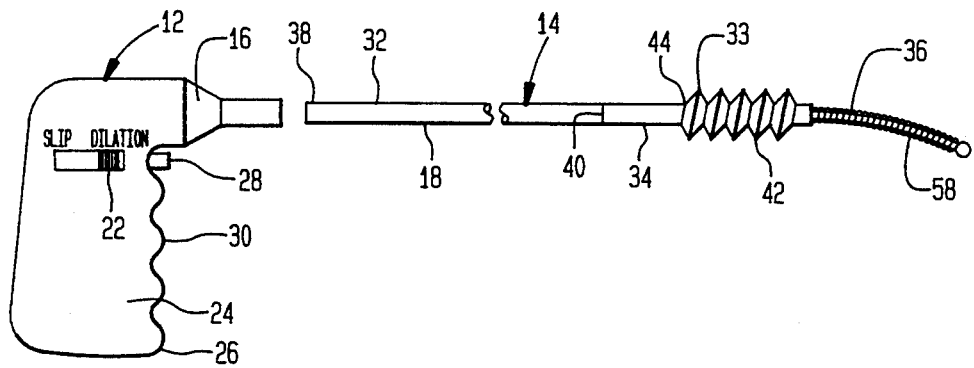
FIG. 1 is an exploded view of a battery operated multifunction ultrasonic wire for angioplasty with the guide wire shown separated from the ultrasonic generator.

Referring now to drawing wherein like reference characters designate like or corresponding parts throughout, there is illustrated in FIG. 1, a battery operated multifunction ultrasonic wire apparatus generally designated as reference numeral 10, particularly well suited for angioplasty, which includes a battery operated ultrasonic generator assembly generally designated 12 and a composite guide wire generally designated 14.

The ultrasonic generator assembly 12 includes an ultrasonic velocity transformer 16 which couples energy directly into the composite guide wire 14 in order to decrease frictional forces between a surface 18 of the composite guide wire 14 and a surface of an inner wall of an arterial vessel, typically during an angioplasty procedure. The ultrasonic generator assembly 12 has the effect of increasing slipperiness along the surface 18 of the composite guide wire 14 while in contact with an inner wall of the arterial vessel and also causing a multi-directional whip-like motion of an end 20 of the composite guide wire 14 which increases probability of crossing high grade lesions.

The ultrasonic generator assembly 12 is capable of operating in two modes. In the first mode of operation, the ultrasonic generator assembly 12 creates uniform slipperiness along the surface 18 of the composite guide wire 14 and whip-like motion as previously described. In the second mode of operation, the ultrasonic generator assembly 12 increases ability of the composite guide wire 14 to dilate the artery or remove plaque. In the second mode of operation, the composite guide wire 14 is capable of increasing the size of vessel lumens by directing cavitational forces into the vessel wall through use of a rasp-like segment 33 or by utilizing ultrasonic motion the segment 33 can file plaque or other build-up in a manner which will described presently.

The modes of operation of the ultrasonic generator assembly 12 are selected through use of a selector switch 22 which is mounted on an outer surface 24 of a housing 26. The housing 26 also includes an on-off switch 28. Depressing the on-off switch 28 directs ultrasonic vibration into the composite guide wire 14. The housing 26 also includes a hand grip portion 30 for convenient grasping of the ultrasonic generator 12 by a medical practitioner typically during an angioplasty procedure.

Figure 3:
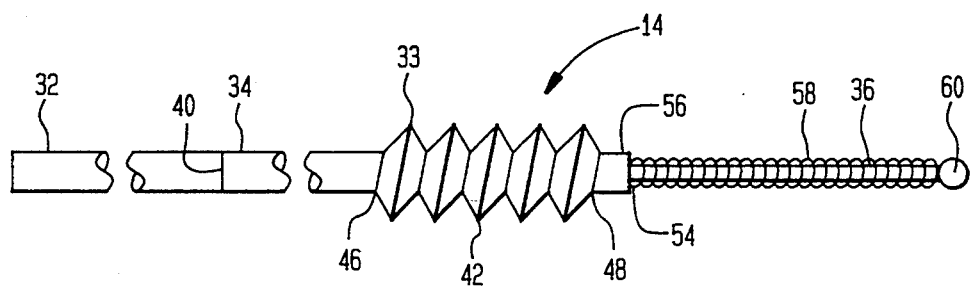
FIG. 3 is an elevation view of the guide wire of FIG. 1.
Figure 4:
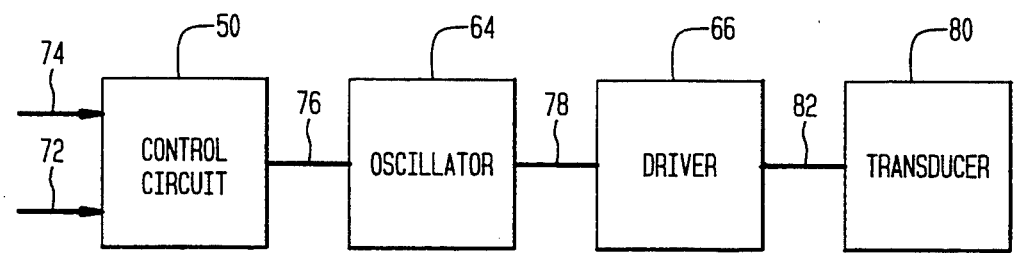
FIG. 4 is a block diagram of an of an electrical circuit for the ultrasonic generator of FIG. 1.

With reference to FIG. 3, the composite guide wire 14 includes a first segment 32 which is located at a proximal near end of the composite guide wire 14 and segments 34 and 36. the segment 36 is located a distal far end of the composite guide wire 14. The segment 32 is made of a relatively stiff material and is the least flexible as compared with the segments 34 and 36 which will described presently. An appropriate material for the segment 32 has been found to be stainless steel.

During use an end 38 of the segment 32 is attached to the velocity transformer 16, and the ultrasonic generator assembly 12. The composite guide wire 14 may be removed from the ultrasonic generator assembly 12 and then used to direct a balloon catheter or other device requiring a flexible guide to the location of a lesion in a vessel as will described presently.

The wire segment 34 is made of a material that is more flexible than the segment 32. An appropriate material for the segment 34 has been found to be titanium. The Segments 32 and 34 are preferably joined together by electron beam welding at an interface 40. The combination of these dissimilar materials, in combination with energy generated by the ultrasonic generator assembly 12, provides different bending characteristics for reaching most remote areas within a human body. The two segments 32 and 34, in combination with the segment 36, transmit ultrasonic forces in the form of mechanical movement to file away plaque or similar build-up and hence increase the lumen size of an artery by filing away plaque to dilate the artery, typically for insertion therein of a balloon catheter or other similar device.

Figure 6:
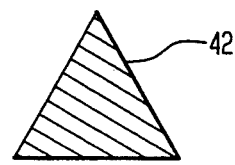
FIG. 6 is a cross sectional view of a triangular cross sectional wire which is wrapped on the guide wire.

The wire segment 34 includes a thin wire 42 having a triangular cross section which is wound over a distal end 44 of the segment 34. The cross section of the wire 42 is shown in FIG. 6. Length of a segment 33, as measured between the locations denoted by reference numerals 46, 48; is equal to a one-quarter wave length of the drive frequency of the ultrasonic generator assembly. With the length of the segment 33 equal to one-quarter of said wave length, a control circuit 50 within the ultrasonic generator assembly 12 can ensure an adequate supply of ultrasonic energy for increasing the lumen of an artery while minimizing overall requirements for ultrasonic energy.

Figure 2:
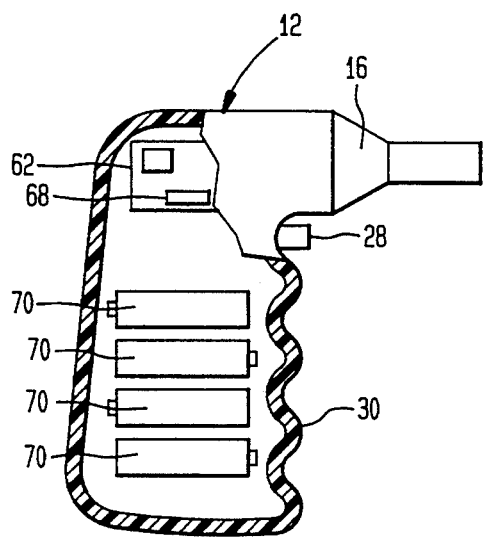
FIG. 2 is a fragmentary cross sectional view showing internal construction of the ultrasonic generator of FIG. 1.

The wire segment 36, as best seen in FIG. 3, is constructed to be extremely soft and flexible and includes a thin central wire 52 which has an end 54 pointed to the end 56 of the segment 34. A hair-like wire 58 is spun around the central wire 52. The segment 36 has a rounded end portion 60 and is so soft that it bends or buckles under its own weight. During operation the segment 36 performs a whipping motion which allows it to pass past or through a high grade occlusion. The degree of whipping motion is controlled by the control circuit 50 within the ultrasonic generator assembly 12 and includes a circuit board 62 (shown in FIG. 2) upon which are mounted the control circuit 50, an oscillator circuit 64 and the driver circuit 66. the control circuit 50, the oscillator circuit 64 and the driver circuit 66 utilize surface mounted components to achieve efficient high current low voltage battery performance. This utilization enables batteries 70 to provide sufficient power adequately to complete an angioplasty procedure and enables the apparatus 10 to function as a multipurpose single use device. This single use feature eliminates the need for sterilization.

The control circuit 50 receives inputs from the selector switch 22 via a lead 72 and a lead 74 via the on-off switch 28. The control circuit 50 is connected to the oscillator circuit 64 via a lead 76. The oscillator circuit 64 is connected to the driver circuit 66 via a lead 78. The driver circuit 66 in turn is connected to the transducer 80 via a lead 82.

The control circuit 50 sends a signal associated with a change in selected use, as controlled by the switch 22, at a relatively slow rate in order to allow the transducer 80 sufficient time to react to the change in selected use. If this information is sent too quickly, the transducer 80 would not have sufficient time to react and there would be a reduction in performance. If this information is sent too slowly, hot spots would develop along the guide wire 14 thereby creating need for cooling.

During use, if the practitioner decides that the slipperiness of the guide wire 14 should be maximized, positioning of the selector switch 22 causes the control circuit 50 to send signals to the oscillator circuit 66 over a relatively greater frequency range. This frequency range is centered about the frequency of the transducer 80 and causes a decrease in frictional forces between the guide wire 14 and the inner walls of the vessel and also causes the segment 36 to whip transversely. This whipping motion increases probability that a high grade lesion can be crossed successfully in an acceptable time period.

If the medical practitioner decides that there is a need to remove plaque or other build-up, the switch 22 is moved to the position marked "Dilation" in FIG. 1 and the control circuit 50 sends signals to the oscillator over a much narrower frequency range. The guide wire 14 in this mode is relatively stiff or robust and is able mechanically to remove plaque build-up or dilate the artery lumen for insertion of other devices typically such as a balloon catheter.

Figure 5:
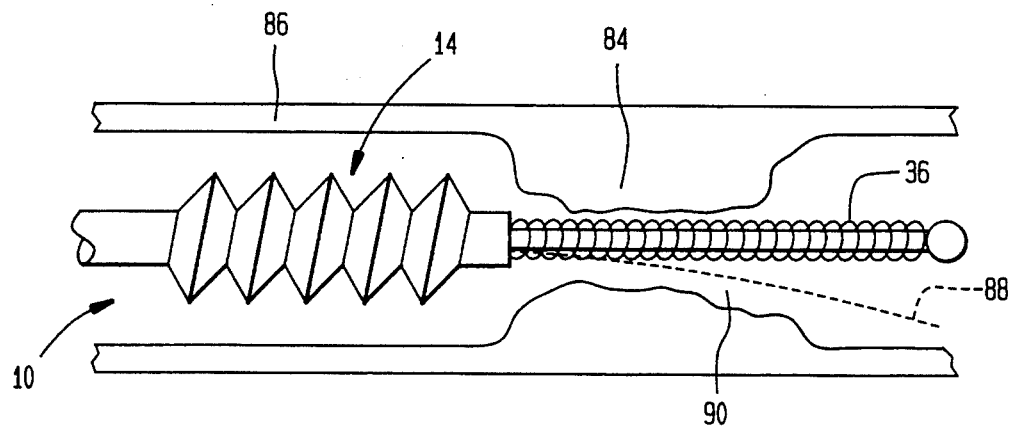
FIG. 5 is a cross sectional view of the guide wire crossing a high grade lesion.

FIG. 5 shows the apparatus 10 in use crossing a lesion 84 in and after wall portion 86. In this mode the selector switch 22 has been moved to the position marked "Slip" in FIG. 1, and the guide wire 14 has a uniform slickness, thereby promoting ease of passage through intricate vessels. The wire segment 36 moves with a whip-like motion in random directions as indicated by the broken line 88 thereby increasing chances that a narrow passage 90 will be crossed, by finding a correct entry angle, in a minimum amount of time. The apparatus 10 is particularly effective when the lesion 84 or plaque deposit or other obstruction is within a curved portion of an artery. The natural tendency of the guide wire 14 to remain straight keeps the guide wire 14 to one side of the artery. With the segment 36 moving in many directions, obscure entry angles can be found thereby reducing difficulty of wire delivery.

Figure 7:
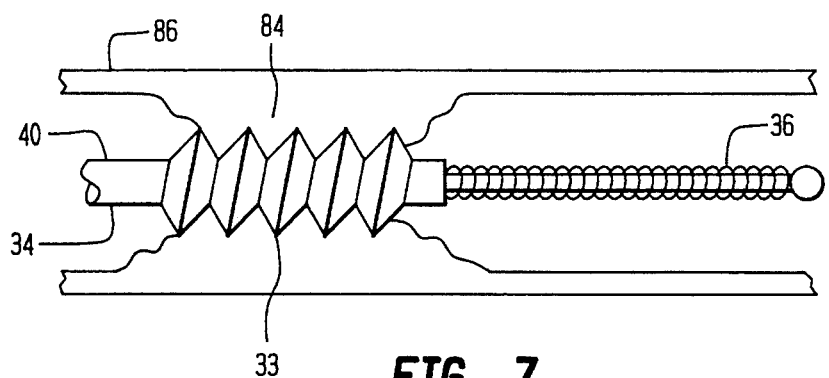
FIG. 7 is a cross sectional view of the guide wire in the process of reducing the build-up of plaque or the like through the mechanical complying of ultrasonic motion.

Once the guide wire 14 has crossed the lesion 84, the guide wire 14 can be positioned such that the rasp-like portion enters the area blocked by the lesion 84 as is shown in FIG. 7. The selector switch 22 is then moved to the position marked "Dilation" and cavitational energy is focused along the rasp-like portion 33 and can be applied to the lesion 84. the wire portion 33 can be used to file away some plaque or other build-up to dilate the artery 86 sufficiently either for further dilation through use of a balloon catheter or for sufficient blood flow through the artery 86.

Figure 8:
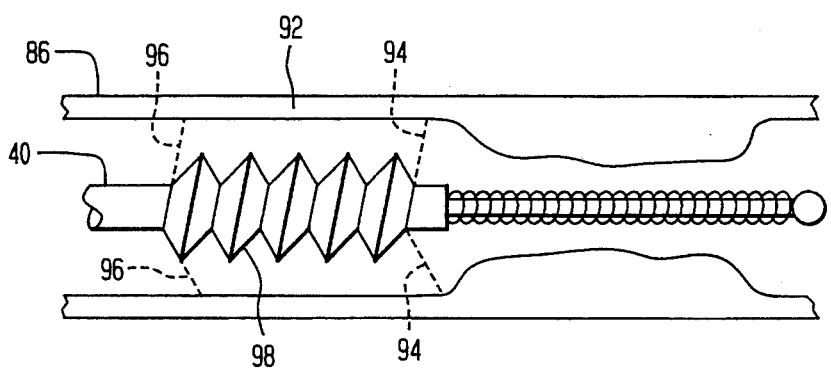
FIG. 8 is a cross sectional view of the guide wire in the process of applying cavitational energy for the dilation of an artery.

FIG. 8 shows another mode of operation of the apparatus 10. In this mode, the triangular shape of the wire 40 focuses ultrasonic cavitational energy onto an arterial wall 92 slightly behind the portion 33 as indicated by broken line 96. The broken lines 94, 96 indicate the area in which the ultrasonic cavitational energy is directed. The angle portions indicated typically by the reference numeral 98 direct energy into the artery 86 thereby dilating the lumen and creating an area of increased lumen size for passage of a balloon catheter 100 (FIG. 9) or for further removal of plaque using the portion 33.

Figure 9:
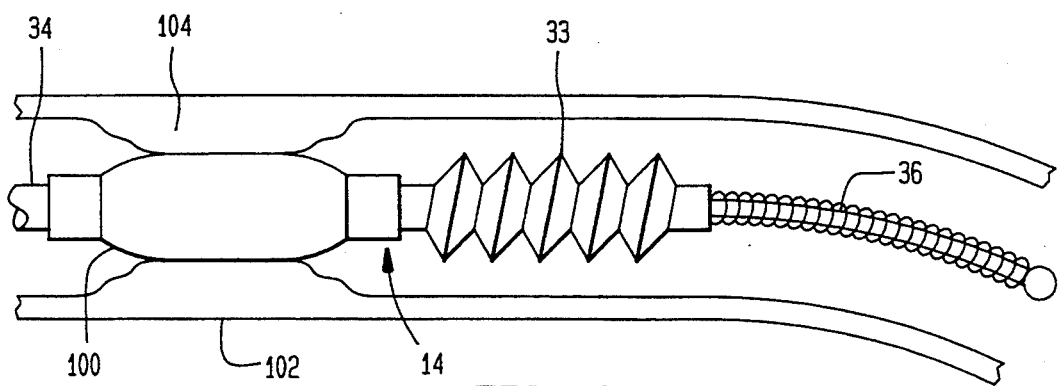
FIG. 9 is a cross sectional view of the guide wire in the process of applying a balloon catheter pressure to a plaque build-up on the inner wall of the artery.

FIG. 9 shows the guide wire 14' having advanced deeper into a vessel at 102. The ultrasonic generator 12 has been removed and the balloon catheter 100 has been directed over the segment 34 in order to operate on a lesion 104. In this mode of operation, the apparatus 10 enables the medical practitioner to direct the balloon catheter 100 in a manner which is known in the field of balloon angioplasty.

It should be understood that the foregoing detailed description relates to a limited number of preferred embodiments of the invention which have been discussed by way of illustration. It is intended to cover all changes and modifications of the examples of the invention herein chosen for the purpose of the disclosure, which do not constitute departures from the spirit and scope of the invention.

I claim:

1. A battery operated multifunction ultrasonic wire for angioplasty comprising:
    ultrasonic generator means capable of generating ultrasonic frequencies;
    ultrasonic wire means comprising a first elongated segment having a proximal end and a distal end;
    a second elongated segment having a proximal end and a distal end;
    a third elongated segment having a proximal end and a distal end, with said first elongated segment having a relatively high stiffness as compared to said second elongated segment and with said third elongated segment having a relatively low stiffness as compared with said second elongated segment; said distal end of said first elongated segment joined to said proximal end of said second elongated segment and said distal end of said second elongated segment joined to said proximal end of said third elongated segment; and
    connection means mounted on said ultrasonic generator means for connection of said ultrasonic generator means to said proximal end of said first elongated segment.

2. The battery operated multifunction ultrasonic wire for angioplasty as claimed in claim 1, wherein said first elongated segment and said second elongated segment are joined to each other by electron beam welding and wherein said second elongated segment and said third elongated segment are joined to each other by electron beam welding.

3. The battery operated multifunction ultrasonic wire for angioplasty as claimed in claim 1, wherein said first elongated segment and said second elongated segment and said third elongated segment are in general alignment.

4. The battery operated multifunction ultrasonic wire for angioplasty as claimed in claim 1, wherein said first elongated segment is made of stainless steel.

5. The battery operated multifunction ultrasonic wire for angioplasty as claimed in claim 1, wherein said second elongated segment is made of titanium.

6. The battery operated multifunction ultrasonic wire for angioplasty as claimed in claim 1, further comprising a wrap wire with said wrap wire wound circumferentially on said second elongated segment proximate to said distal end of said second elongates segment.

7. The battery operated multifunction ultrasonic wire for angioplasty as claimed in claim 6, wherein said wrap wire has a triangular cross section.

8. The battery operated multifunction ultrasonic wire for angioplasty as claimed in claim 6, wherein said wrap wire is wound on said second elongated segment forming a wirewound portion having a plurality of spiraling turns, with said wirewound portion having a length equal to one-quarter wave length of a selected one of said ultrasonic frequencies generated by said ultrasonic generator.

9. The battery operated multifunction ultrasonic wire for angioplasty as claimed in claim 1, wherein said third elongated segment comprises a thin wire.

10. The battery operated multifunction ultrasonic wire for angioplasty as claimed in claim 9, wherein said third elongated segment comprises a flexible wire core and a band wire wrapped around said wire core.

11. A battery operated multifunction ultrasonic wire for angioplasty as claimed in claim 1, wherein said ultrasonic generator means comprises selector switch means and wherein said ultrasonic generator is capable of generating selectively ultrasonic energy having a relatively broad frequency range and generating ultrasonic energy having a relatively narrow frequency range with said selector switch means capable of selecting between said frequency ranges.

12. A battery operated wire, especially suited for intravascular surgical procedures wherein a circulatory vessel is at least partially occluded by an obstruction leaving a restricted lumen at the obstruction, the wire comprising in combination:

generator means for generating selectively ultrasonic energy having either a broad frequency range or a narrow frequency range with selector switch means for selecting therebetween;

a first wire segment having a first proximal end and first distal end, a second wire segment having a second proximal end and a second distal end, and a third wire segment having a third proximal end and a third distal end, with the three wire segments in general alignment;

the first segment having a relatively high stiffness as compared to that of the second segment and the third segment being thin and having a relatively low stiffness as compared with that of the second segment;

the first distal end joined to second proximal end and the second distal end joined to the third proximal end;

connection means for connecting the generator means to the first proximal end;

a wrap wire wound on the second distal end, the second distal end having a length equal to approximately one-quarter wave length of the second frequency range;

whereby with the selector switch means selecting the first frequency range, the third segment whips randomly to find and get through the restricted lumen and whereby with the selector switch means selecting the second frequency range and the second distal end positioned in the lumen dislodging mechanically clot and/or plaque and/or other debris from the lumen and/or to dilate the vessel.

13. The battery operated wire as claimed in claim 12, wherein the third segment has a band wire wrapped therearound.

14. The battery operated wire as claimed in claim 12, wherein the segments are joined by means of electron beam welding.

15. The battery operated wire as claimed in claim 12, wherein the first segment is made of stainless steel.

16. The battery operated wire as claimed in claim 12, wherein the second segment is made of titanium.

17. The battery operated wire as claimed in claim 12, wherein the wrap wire is triangular in cross-section.

* * * * *